(12) United States Patent
Choinski et al.

(10) Patent No.: US 10,918,429 B2
(45) Date of Patent: Feb. 16, 2021

(54) FRACTURE FIXATION SYSTEM INCLUDING LOCKING CAP AND WIRE

(71) Applicant: ARTHREX, INC., Naples, FL (US)

(72) Inventors: Ronald J. Choinski, Fort Myers Beach, FL (US); Thomas E. Trumble, Mercer Island, WA (US)

(73) Assignee: ARTHREX, INC., Naples, FL (US)

( * ) Notice: Subject to any disclaimer, the term of this patent is extended or adjusted under 35 U.S.C. 154(b) by 98 days.

(21) Appl. No.: 16/121,688

(22) Filed: Sep. 5, 2018

(65) Prior Publication Data

US 2019/0000520 A1  Jan. 3, 2019

Related U.S. Application Data

(63) Continuation of application No. 14/564,509, filed on Dec. 9, 2014, now Pat. No. 10,092,340.

(51) Int. Cl.
*A61B 17/86* (2006.01)
*A61B 17/80* (2006.01)

(52) U.S. Cl.
CPC ...... *A61B 17/8625* (2013.01); *A61B 17/8057* (2013.01); *A61B 2017/867* (2013.01)

(58) Field of Classification Search
CPC ..... A61B 17/80; A61B 17/8033; A61B 17/86; A61B 17/8665; A61B 17/88; A61B 17/8861

See application file for complete search history.

(56) References Cited

U.S. PATENT DOCUMENTS

| 5,607,428 | A | * | 3/1997 | Lin | A61B 17/8047 606/287 |
| 5,709,687 | A | * | 1/1998 | Pennig | A61B 17/80 411/368 |
| 5,931,839 | A | | 8/1999 | Medoff | |
| 6,440,135 | B2 | | 8/2002 | Orbay et al. | |
| 7,044,951 | B2 | * | 5/2006 | Medoff | A61B 17/80 606/281 |
| 7,195,633 | B2 | | 3/2007 | Medoff et al. | |
| 7,527,639 | B2 | | 5/2009 | Orbay et al. | |
| 7,780,711 | B2 | | 8/2010 | Orbay et al. | |
| 7,883,531 | B2 | * | 2/2011 | de Coninck | A61B 17/7059 606/290 |
| 7,931,681 | B2 | | 4/2011 | Carls et al. | |
| 8,636,777 | B2 | * | 1/2014 | Jackson | A61B 17/7037 606/279 |
| 8,753,379 | B1 | * | 6/2014 | Frei | A61B 17/1735 606/288 |
| 10,092,340 | B2 | * | 10/2018 | Choinski | A61B 17/8057 |
| 2006/0235402 | A1 | | 10/2006 | Celli et al. | |
| 2008/0021475 | A1 | | 1/2008 | Lawrie | |
| 2008/0114359 | A1 | * | 5/2008 | Murner | A61B 17/8033 606/66 |

(Continued)

*Primary Examiner* — Christopher J Beccia
(74) *Attorney, Agent, or Firm* — Carlson, Gaskey & Olds

(57) ABSTRACT

A locking cap for a fracture fixation system according to an exemplary aspect of the present disclosure includes, among other things, a cap body that extends along a longitudinal axis between a proximal end and a distal end. An external thread extends around at least a portion of the cap body. A passage extends inside the cap body from the distal end toward the proximal end. An internal thread extends about a periphery of the passage along at least a portion of a length of the passage.

18 Claims, 4 Drawing Sheets

(56) References Cited

U.S. PATENT DOCUMENTS

| | | |
|---|---|---|
| 2011/0029025 A1 | 2/2011 | Medoff |
| 2011/0106172 A1* | 5/2011 | Wallenstein ....... A61B 17/8605 606/286 |
| 2011/0264149 A1 | 10/2011 | Pappalardo et al. |
| 2013/0190825 A1 | 7/2013 | Perrow et al. |
| 2014/0107710 A1 | 4/2014 | Forderer et al. |

* cited by examiner

FRACTURE FIXATION SYSTEM INCLUDING LOCKING CAP AND WIRE

CROSS REFERENCE TO RELATED APPLICATION

This is a continuation of U.S. patent application Ser. No. 14/564,509, filed on Dec. 9, 2014, the disclosure of which is incorporated herein by reference in its entirety.

BACKGROUND

This disclosure relates to a fracture fixation system for repairing bone fractures. The fracture fixation system includes a locking cap having internal threads configured to engage a wire and external threads configured to engage a bone plate.

Bone deformities can develop if a bone fracture is not adequately repaired. Fracture fixation systems are commonly used to align and fixate bone fragments to reconstruct a fractured bone. One known fracture fixation system includes a bone plate and multiple fasteners that are inserted through openings in the bone plate to fasten the bone plate to bone on both sides of the fracture. The fracture fixation system may additionally use wires to provisionally stabilize the bone fragments during a repair.

SUMMARY

A locking cap for a fracture fixation system according to an exemplary aspect of the present disclosure includes, among other things, a cap body that extends along a longitudinal axis between a proximal end and a distal end. An external thread extends around at least a portion of the cap body. A passage extends inside the cap body from the distal end toward the proximal end. An internal thread extends about a periphery of the passage along at least a portion of a length of the passage.

In a further non-limiting embodiment of the foregoing locking cap, the proximal end tapers toward the distal end.

In a further non-limiting embodiment of either of the foregoing locking caps, the cap body is configured to include a screw head shape.

In a further non-limiting embodiment of any of the foregoing locking caps, a driver recess is disposed at the proximal end of the cap body.

In a further non-limiting embodiment of any of the foregoing locking caps, the internal thread is unconnected to the driver recess.

In a further non-limiting embodiment of any of the foregoing locking caps, the passage extends entirely through the cap body.

In a further non-limiting embodiment of any of the foregoing locking caps, the passage includes the internal thread at the distal end and a non-threaded portion at the proximal end.

In a further non-limiting embodiment of any of the foregoing locking caps, the non-threaded portion establishes a driver recess.

In a further non-limiting embodiment of any of the foregoing locking caps, the passage extends along the longitudinal axis of the cap body.

In a further non-limiting embodiment of any of the foregoing locking caps, the external thread is configured as a variable angle locking thread.

A fracture fixation system according to another exemplary aspect of the present disclosure includes, among other things, a bone plate having a plurality of threaded openings, a locking cap threadably secured within one of the plurality of threaded openings and a wire threadably attached to the locking cap.

In a further non-limiting embodiment of the foregoing system, the wire includes a threaded portion and a non-threaded portion.

In a further non-limiting embodiment of either of the foregoing systems, the wire is a K-wire.

In a further non-limiting embodiment of any of the foregoing systems, the locking cap includes a passage having an internal thread, the wire including a threaded portion configured to engage the internal thread.

In a further non-limiting embodiment of any of the foregoing systems, the passage includes a non-threaded portion proximal of the internal thread.

A surgical method according to another exemplary aspect of the present disclosure includes, among other things, threading a locking cap onto a threaded portion of a wire and advancing the locking cap along the threaded portion until the locking cap threads into a threaded opening of a bone plate to secure the wire relative to the bone plate.

In a further non-limiting embodiment of the foregoing method, the method includes, prior to the threading and advancing steps, inserting the wire to a desired depth in a fractured bone, the wire extending through the threaded opening of the bone plate.

In a further non-limiting embodiment of either of the foregoing methods, the method includes sliding the locking cap along a non-threaded portion of the wire prior to the threading step.

In a further non-limiting embodiment of any of the foregoing methods, the method includes, prior to the threading and advancing steps, inserting the wire through the threaded opening of the bone plate and into a fractured bone and sliding the locking cap along a non-threaded portion of the wire toward the threaded portion.

In a further non-limiting embodiment of any of the foregoing methods, the method includes cutting the wire flush with a proximal end of the locking cap.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure relates to a fracture fixation system for treating a fractured bone. The fracture fixation system includes a locking cap configured to connect a wire to a bone plate of the fracture fixation system. An exemplary locking cap includes a cap body having an external thread for threading the locking cap into an opening of the bone plate, and an internal thread for receiving a threaded portion of the wire. The locking cap may be secured at various angles within the opening of the bone plate. The locking cap of the fracture fixation system rigidly secures the wire to the bone plate to promote improved fragment stability and reduced tissue irritation. These and other features are discussed in greater detail in the following paragraphs.

Figure 1:
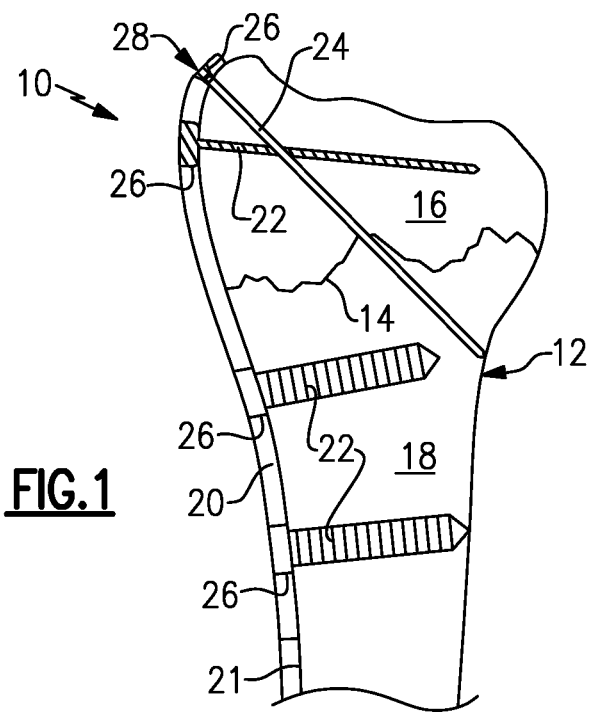
FIG. 1 illustrates a fracture fixation system.

FIG. 1 illustrates a fracture fixation system 10 that may be employed during a surgical procedure to repair a fractured bone 12. The fractured bone 12 includes a fracture 14 that divides the fractured bone 12 into at least a first bone fragment 16 and a second bone fragment 18. Although two bone fragments 16, 18 are illustrated in this embodiment, the fractured bone 12 could include any number of bone fragments.

In one non-limiting embodiment, the fractured bone 12 is a distal radius bone of a human wrist joint. However, this disclosure is not limited to this example. The fracture fixation system 10 could be utilized to repair any fractured bone located anywhere within a human or animal body.

In one non-limiting embodiment, the fracture fixation system 10 includes a bone plate 20, a plurality of fasteners 22, and one or more wires 24. The bone plate 20 is sized and shaped for positioning against an exterior surface 21 of the fractured bone 12. The actual size and shape of the bone plate 20 may vary depending on the type of bone being treated, among other factors.

In one embodiment, the bone plate 20 is made of a metallic material. Non-limiting examples of suitable metallic materials include titanium, stainless steel, and cobalt. In other embodiments, the bone plate 20 could be made of carbon fiber or plastic based materials.

The bone plate 20 may include a plurality of threaded openings 26 that extend through the bone plate 20. Each threaded opening 26 can receive one of the fasteners 22. The bone plate 20 may include any amount of threaded openings 26 for securing the bone plate 20 to the fractured bone 12 using the fasteners 22. The fasteners 22 may extend through one of the threaded openings 26 and into the fractured bone 12. The fasteners 22 may extend into either the first bone fragment 16 or the second bone fragment 18 of the fractured bone 12. In one embodiment, the fasteners 22 are screws. The fasteners 22 may include different sizes, shapes and configurations.

The wire 24 of the fracture fixation system 10 may also be passed through one of the threaded openings 26 of the bone plate. Although a single wire 24 is illustrated in FIG. 1, the fracture fixation system 10 could employ multiple wires 24 to repair the fractured bone 12. The wire 24 may be inserted into the fractured bone 12 and may extend into one or both of the first bone fragment 16 and the second bone fragment 18. The wire 24 provisionally fixates the first bone fragment 16 at a desired position relative to the second bone fragment 18 and stabilizes the bone fragments 16, 18 during the fracture fixation procedure. In one non-limiting embodiment, the wire 24 is a K-wire. The wire 24 may embody any size. The actual size of the wire 24 may depend on the type of bone being repaired, among other factors.

In one embodiment, the wire 24 is secured to the bone plate 20 by a locking cap 28. The locking cap 28 may be threadably secured within the threaded opening 26 that receives the wire 24. The locking cap 28 is designed to prevent the wire 24 from backing out of the bone fragments 16, 18 through the threaded opening 26. In this manner, the locking cap 28 protects surrounding tissue from irritation that can occur in prior art fracture fixation systems when the wire 24 backs out of the bone fragments 16, 18.

In another non-limiting embodiment, the locking cap 28 can be installed in the bone plate 20 at variable angles along variable axes to secure the locking cap 28 to the bone plate 20. For example, both the locking cap 28 and the threaded openings 26 of the bone plate 20 may be configured with threads that allow for multiples threads of engagement. In one non-limiting embodiment, the angle of the locking cap 28 can vary from between 0 degrees and about 10 degrees in any direction relative to a central axis of the threaded opening 26.

Figure 2A:
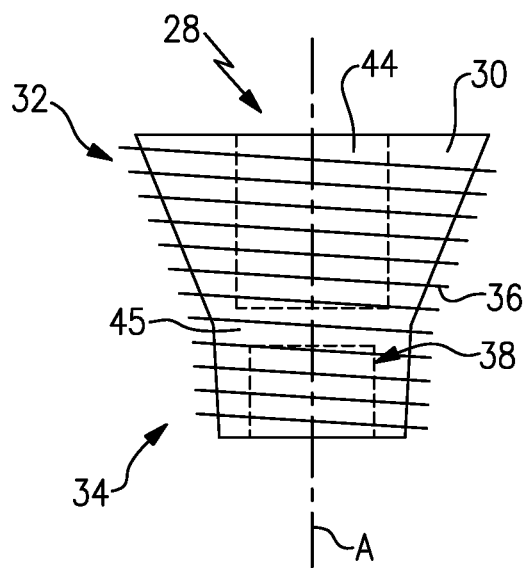
FIGS. 2A and 2B illustrate a locking cap according to a first embodiment of this disclosure.
Figure 2B:
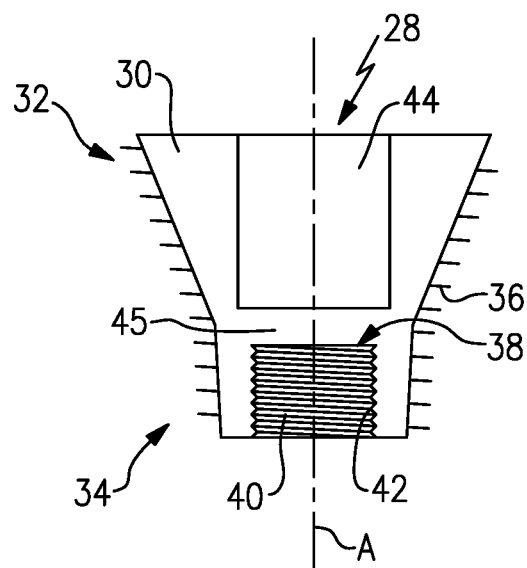

FIGS. 2A and 2B illustrate an exemplary locking cap 28 of the fracture fixation system 10. The locking cap 28 includes a cap body 30 that extends along a longitudinal axis A between a proximal end 32 and a distal end 34. In one embodiment, the proximal end 32 at least partially tapers toward the distal end 34 such that the locking cap 28 defines a "screw head" shape. Other shapes are also contemplated within the scope of this disclosure.

An external thread 36 extends around at least a portion of the cap body 30. The external thread 36 is a male thread configured to threadably secure the locking cap 28 within one of the threaded openings 26 of the bone plate 20 (as shown, for example, in FIG. 1). The major diameter, minor diameter, pitch and other design characteristics of the external thread 36 are not intended to limit this disclosure.

A passage 38 may extend inside of the cap body 30 along the longitudinal axis A. In one embodiment, the passage 38 extends from the distal end 34 of the cap body 30 toward the proximal end 32. A portion of the passage 38 can include an internal thread 40 that extends circumferentially about a periphery 42 of the passage 38 (best illustrated in cross-sectional view of FIG. 2B). The internal thread 40, which may be a female thread, is configured to threadably receive a threaded portion of a wire 24 (see FIG. 1), as discussed in greater detail below.

The cap body 30 may additionally include a driver recess 44. The driver recess 44 is un-threaded. A solid portion 45 of the cap body 30 may extend between the passage 38 and the driver recess 44 such that the driver recess 44 is unconnected to the passage 38. In other words, the cap body 30 is not fully cannulated in this embodiment. In one embodiment, the driver recess 44 extends from the proximal end 32 toward the distal end 34 of the cap body 30.

Figure 3:
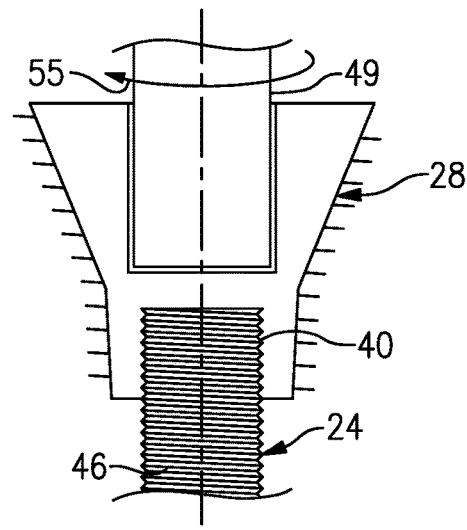
FIG. 3 illustrates a locking cap and a wire of a fracture fixation system.

Referring now to FIG. 3, the driver recess 44 of the cap body 30 of the locking cap 28 may receive a driver 49 for screwing the locking cap 28 onto the wire 24. The wire 24 includes a threaded portion 46 that is threaded into the internal thread 40 as the driver 49 is rotated as schematically illustrated by arrow 55.

Figure 4:
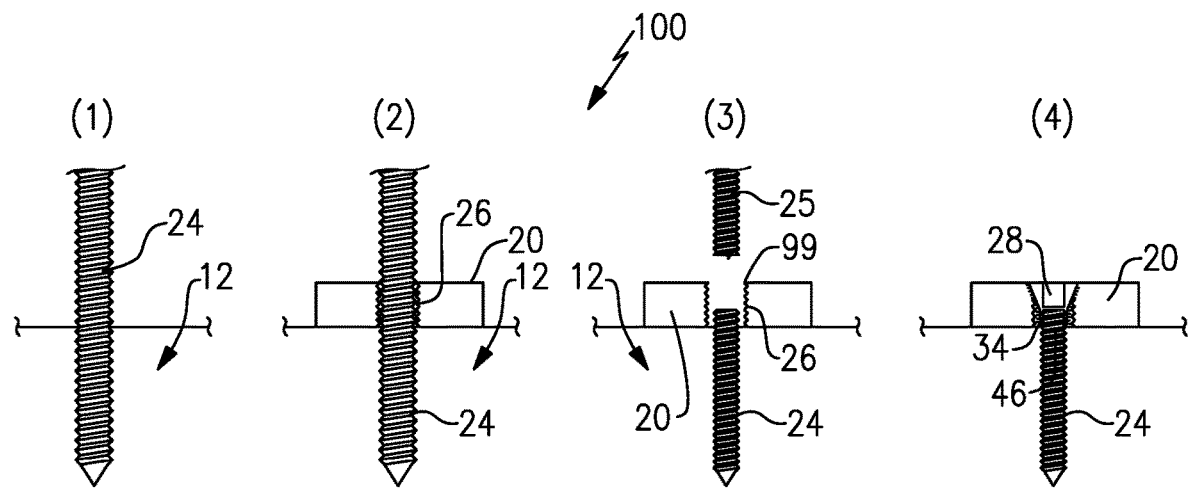
FIG. 4 illustrates an exemplary surgical method for repairing a fractured bone.

FIG. 4, with continued reference to FIGS. 1, 2 and 3, illustrates a surgical method 100 for repairing a fractured bone 12 using the fracture fixation system 10. As shown in picture (1), the wire 24 is inserted to a desired depth into the fractured bone 12. The wire 24 may or may not traverse the fracture 14 of the fractured bone 12 (see FIG. 1). Therefore, the wire 24 could extend into only the first bone fragment 16, only the first bone fragment 18, or into both of the first bone fragment 16 and the second bone fragment 18.

Next, as shown in picture (2), the bone plate 20 is positioned against the fractured bone 12. The bone plate 20 may be received over the wire 24 such that the wire 24 extends through a threaded opening 26 of the bone plate 20. In an alternative embodiment, the steps shown in pictures (1) and (2) can performed in a reversed order in which the bone plate 20 is positioned relative to the fractured bone 12 before the wire 24 is inserted into the fractured bone 12.

As shown in picture (3), a portion 25 of the wire 24 may be cut so the wire 24 does not protrude outside of the threaded opening 26 of the bone plate 20. Any cutting tool may be used to cut the wire 24. In one embodiment, the wire 24 is cut so that it extends distally from a proximal portion 99 of the threaded opening 26.

Finally, as shown in picture (4), the locking cap 28 is threaded onto the threaded portion 46 of the wire 24 and advanced until the locking cap 28 threads into the threaded opening 26 of the bone plate 20 to secure the wire 24 relative to the bone plate 20. In one embodiment, distal end 34 of the locking cap 28 does not extend out of the threaded opening 26 into the fractured bone 12. The locking cap 28 locks the wire 24 into place and substantially prevents the wire 24 from backing out of the fractured bone 12.

Figure 5A:
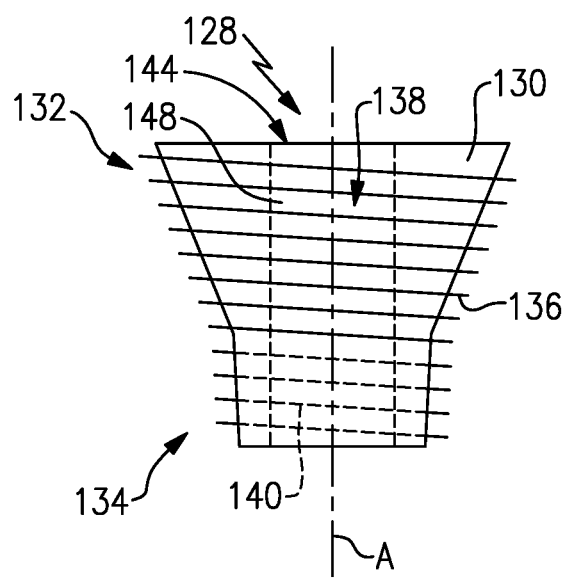
FIGS. 5A and 5B illustrate a locking cap according to a second embodiment of this disclosure.
Figure 5B:
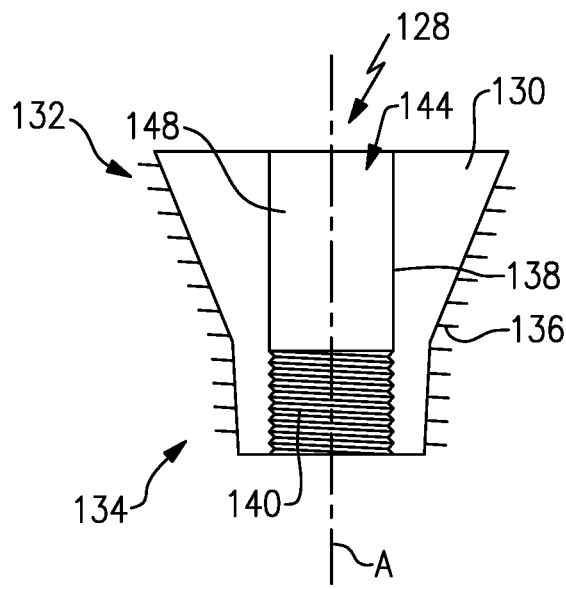

FIGS. 5A and 5B illustrate a locking cap 128 according to another embodiment of this disclosure. In this disclosure, like reference numbers designate like elements where appropriate and reference numerals with the addition of 100 or multiples thereof designate modified elements that are understood to incorporate the same features and benefits of the corresponding original elements In this embodiment, the locking cap 128 includes a cap body 130 that extends along a longitudinal axis A between a proximal end 132 and a distal end 134. The proximal end 132 may taper toward the distal end 134 to define a "screw head" shape of the locking cap 128. An external thread 136 wraps around at least a portion of the cap body 130. The external thread 136 is a male thread configured to threadably secure the locking cap 128 within one of the threaded openings 26 of the bone plate 20, as illustrated in greater detail in FIG. 7. In one non-limiting embodiment, the external thread 136 is configured as a variable angle locking thread that is capable of being secured within a matching threaded opening of a bone plate at variable angles along variable axes.

A passage 138 may extend inside of the cap body 130 along the longitudinal axis A. In one embodiment, the cap body 130 is fully cannulated such that the passage 138 extends entirely through the cap body 130 from the distal end 134 to the proximal end 132. The passage 138 may include an internal thread 140 and a non-threaded portion 148. The internal thread 140, which may be a female thread, is configured to threadably receive a threaded portion of a wire, as discussed below. The non-threaded portion 148 of the passage 138 may establish a driver recess 144. In one non-limiting embodiment, the driver recess 144 is any part of the passage 138 that extends proximally of the threaded portion 140.

Figure 6:
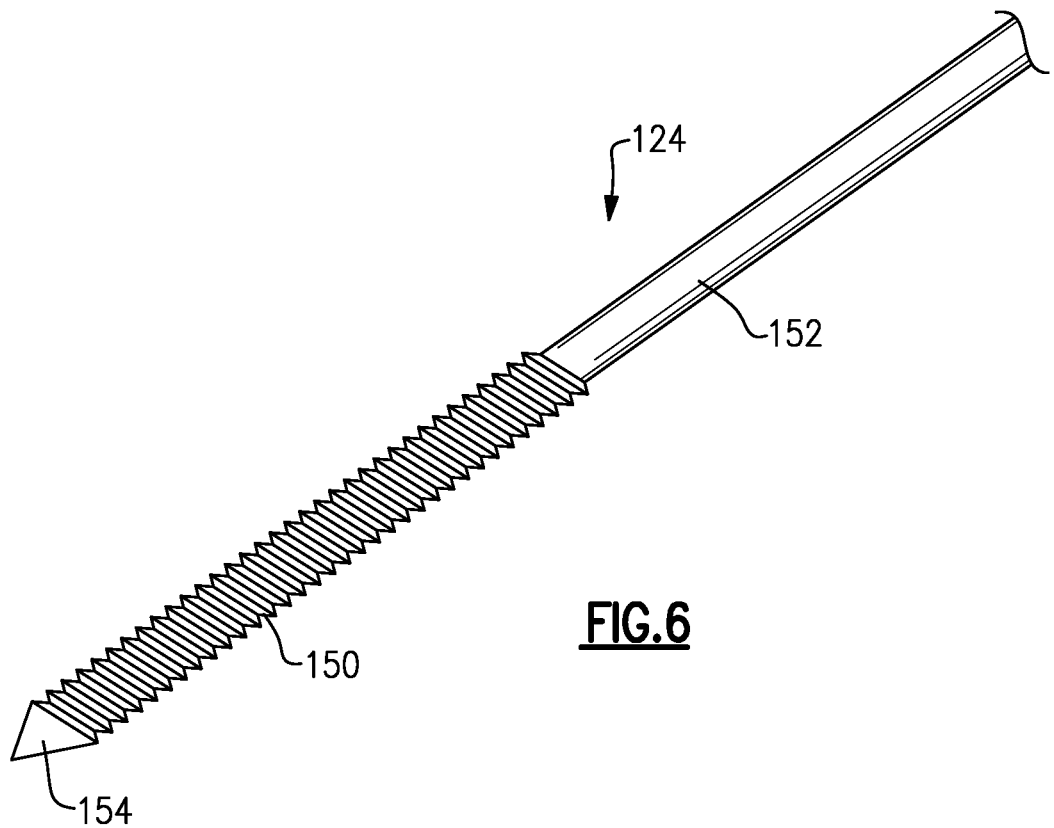
FIG. 6 illustrates a wire of a fracture fixation system.

FIG. 6 illustrates a wire 124 that can be utilized with the locking cap 128 of FIGS. 5A and 5B. In one embodiment, the wire 124 includes a threaded portion 150, located distally, and a non-threaded portion 152, located proximally. The threaded portion 150 may extend to a trocar tip 154. The trocar tip 154 may be pointed to facilitate insertion of the wire 124 into bone. The threaded portion 150 may be configured as a male thread for insertion into the internal thread 140 of the locking cap 128 (see, for example, FIG. 5B). The non-threaded portion 152 of the wire 124 is proximal to the threaded portion 150. The non-threaded portion 152 provides a relatively smooth surface for sliding the locking cap 128 along the wire 124 until it engages the threaded portion 150 (see FIG. 7).

Figure 7:
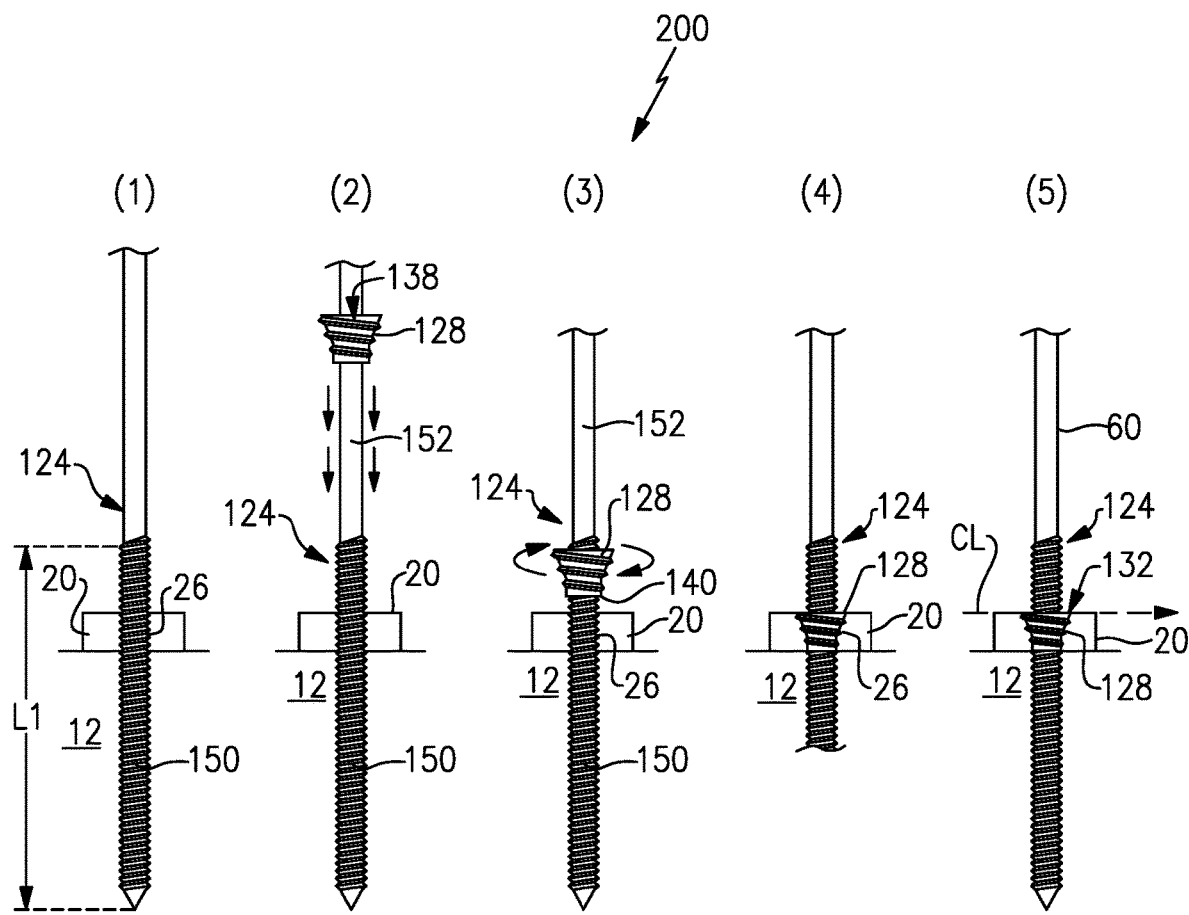
FIG. 7 illustrates another exemplary surgical method for repairing a fractured bone.

FIG. 7, with continued reference to FIGS. 5A, 5B and 6, illustrates a surgical method 200 for repairing a fractured bone 12. The wire 124 is inserted through a threaded opening 26 of a bone plate 20 to a desired depth within the fractured bone 12, as shown in picture (1). The wire 124 may be driven into the fractured bone 12 using known tools, such as a wire driver. The bone plate 20 may be positioned against the fractured bone 12 either before or after insertion of the wire 124 into the fractured bone 12. In either situation, the wire 124 is inserted through the threaded opening 26 of the bone plate 20. The wire 124 generally includes a small diameter than the threaded opening 26. In one embodiment, the threaded portion 150 of the wire 124 includes a length L1 that is large enough to extend out of the threaded opening 26 to a position that is proximal of the bone plate 20. In other words, the wire 124 must be threaded where the locking cap 128 interfaces with the bone plate 20 in order for the locking cap 128 to lock the wire 124 relative to the bone plate 20.

As shown in picture (2), the locking cap 128 is next slid over the non-threaded portion 152 of the wire 124 toward the threaded portion 150. The non-threaded portion 152 may be received within the passage 138 of the locking cap 128. Although not shown, a cannulated driver may be used to insert the locking cap 128 onto the wire 124.

The locking cap 128 may be advanced along the non-threaded portion 152 until it engages the threaded portion 150, which is illustrated in picture (3). The locking cap 128 may be advanced along the threaded portion 150 via rotation until it locks into the threaded opening 26 of the bone plate 20. The threaded portion 150 includes threads that match the internal thread 140 of the locking cap 128.

A fully inserted locking cap 128 is illustrated in picture (4). In the fully inserted position shown in picture (4), the locking cap 128 is locked within the threaded opening 26 to secure the wire 124 relative to the bone plate 20. As shown in picture (5), a portion 60 of the wire 124 may protrude outwardly of the locking cap 128 and bone plate 20. The wire 124 may be cut along a cutting line CL to remove the portion 60. In one embodiment, the wire 124 is cut flush with a proximal end 132 of the locking cap 128. Cutting the wire 124 flush in this manner substantially prevents the wire 124 from irritating surrounding soft tissue. At this point, the wire 124 is essentially transformed into a locking screw that provides rigid fixation in combination with the bone plate 20. The surgical method 200 may then be completed by securing one or more fasteners 22 into other threaded openings 26 of the bone plate 20 (see, for example, FIG. 1).

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A fracture fixation system, comprising:
a bone plate having a plurality of threaded openings;
a locking cap threadably secured within one of said plurality of threaded openings; and
a wire threadably attached to said locking cap,
wherein said locking cap includes a passage having an internal thread and a non-threaded portion proximal of said internal thread,
wherein said internal thread includes a first diameter and said non-threaded portion includes a second diameter that is different from said first diameter,
wherein said internal thread and said non-threaded portion are unconnected to one another.

2. The system as recited in claim 1, wherein said wire includes a threaded portion located distally and a non-threaded portion located proximally.

3. The system as recited in claim 2, wherein said threaded portion extends to a trocar tip.

4. The system as recited in claim 3, wherein said trocar tip is pointed.

5. The system as recited in claim 1, wherein said wire is a K-wire.

6. The system as recited in claim 1, wherein said wire includes a threaded portion configured to engage said internal thread.

7. A surgical method, comprising:
threading the locking cap of claim 1 onto a threaded portion of the wire; and
advancing the locking cap along the threaded portion until the locking cap threads into one of the plurality of threaded openings of the bone plate to secure the wire relative to the bone plate.

8. The method as recited in claim 7, comprising, prior to the threading and advancing steps:
inserting the wire to a desired depth in a fractured bone, the wire extending through the one of the plurality of threaded openings of the bone plate.

9. The method as recited in claim 7, comprising:
sliding the locking cap along a non-threaded portion of the wire prior to the threading step.

10. The method as recited in claim 7, comprising, prior to the threading and advancing steps:
inserting the wire through the one of the plurality of threaded openings of the bone plate and into a fractured bone; and
sliding the locking cap along a non-threaded portion of the wire toward the threaded portion.

11. The method as recited in claim 7, comprising cutting the wire flush with a proximal end of the locking cap.

12. A fracture fixation system, comprising:
a bone plate having a first threaded opening and a second threaded opening;
a screw secured within said first threaded opening;
a locking cap threadably secured within said second threaded opening and including a driver recess and an internal thread;
a driver receivable within said driver recess of said locking cap; and
a k-wire threadably attachable to said internal thread of said locking cap,
wherein said internal thread is unconnected to said driver recess.

13. The system as recited in claim 12, wherein said k-wire includes a threaded portion and a non-threaded portion proximal of said threaded portion.

14. The system as recited in claim 13, wherein said threaded portion extends to a pointed trocar tip.

15. The system as recited in claim 12, wherein a solid portion of said locking cap extends between said internal thread and said driver recess.

16. The system as recited in claim 12, wherein said locking cap includes a variable angle locking external thread.

17. The system as recited in claim 1, wherein said non-threaded portion establishes a driver recess, and further wherein said fracture fixation system comprises a driver receivable within said driver recess.

18. The system as recited in claim 1, wherein said internal thread includes a first length and said non-threaded portion includes a second length that is greater than said first length.

* * * * *